US00PP13073P2

(12) United States Plant Patent
Glicenstein et al.

(10) Patent No.: US PP13,073 P2
(45) Date of Patent: Oct. 15, 2002

(54) AZALEA PLANT NAMED 'SCARLET'

(75) Inventors: Leon Glicenstein, Lebanon, IN (US); Wendy R. Bergman, Lehigh Acres, FL (US)

(73) Assignee: Yoder Brothers, Inc., Barberton, OH (US)

( * ) Notice: Subject to any disclaimer, the term of this patent is extended or adjusted under 35 U.S.C. 154(b) by 46 days.

(21) Appl. No.: 09/888,802

(22) Filed: Jun. 25, 2001

(51) Int. Cl.[7] ..... A01H 5/00
(52) U.S. Cl. ..... Plt./240

(58) Field of Search ..... Plt./240, 239, 238

*Primary Examiner*—Kent L. Bell
(74) *Attorney, Agent, or Firm*—C. A. Whealy

(57) ABSTRACT

A new and distinct cultivar of Azalea plant named 'Scarlet', characterized by its small and very dark green glossy leaves that do not abscise during the cooling and forcing periods; large plants with dense and outwardly spreading plant habit; vigorous growth habit; very freely branching habit; rapid flowering response; numerous, large and showy rich red-colored flowers; semi-double flower form; ruffled petal margins; excellent postproduction longevity; and low incidence of infection with Cylindrocladium in inoculated trials.

2 Drawing Sheets

BACKGROUND OF THE INVENTION

The present Invention relates to a new and distinct cultivar of Azalea, botanically known as *Rhododendron hybrida*, an evergreen greenhouse-forcing type Azalea, and hereinafter referred to by the name 'Scarlet'.

The new Azalea is a product of a planned breeding program conducted by the Inventors in Salinas, Calif. and Alva, Fla. The objective of the breeding program is to create new Azalea varieties having uniform plant habit, profuse and uniform flowering, dark green foliage, good foliage retention during the cooling and forcing periods, resistance to Cylindrocladium, and excellent postproduction longevity.

The new Azalea originated from a cross made by the Inventors in November, 1992, in Salinas, Calif., of a proprietary Azalea seedling selection identified as YB-0335, not patented, as the female, or seed, parent with a proprietary Azalea seedling selection identified as YB-0815, not patented, as the male, or pollen, parent. The new Azalea was discovered and selected by the Inventors as a flowering plant within the progeny of the stated cross in a controlled environment in Alva, Fla., in May, 1995. The selection of this plant was based on its semi-double flower form, rich red flower color, ruffled petal margins, very large flower size, uniform flowering response, very good foliage retention, and excellent postproduction longevity.

Asexual reproduction of the new Azalea by terminal cuttings taken in a controlled environment in Alva, Fla. since October, 1995, has shown that the unique features of this new Azalea are stable and reproduced true to type in successive generations.

SUMMARY OF THE INVENTION

The new Azalea has not been observed under all possible environmental conditions. The phenotype may vary somewhat with variations in environment such as temperature, daylength, light intensity, relative humidity, fertilizer rate and type, and/or water status without, however, any variance in genotype.

The following traits have been repeatedly observed and are determined to be the unique characteristics of 'Scarlet'.

These characteristics in combination distinguish 'Scarlet' as a new and distinct cultivar:

1. Small and very dark green glossy leaves that do not abscise during the cooling and forcing periods.
2. Large plants with dense and outwardly spreading plant habit; vigorous growth habit.
3. Very freely branching habit; usually about 4 or 5 lateral branches develop after pinching.
4. Rapid flowering response; plants begin flowering about 25 days after cooling treatment.
5. Numerous, large and showy rich red-colored flowers.
6. Semi-double flower form.
7. Ruffled petal margins.
8. Excellent postproduction longevity with plants maintaining good flower substance for about four weeks in an interior environment.
9. Low incidence of infection with Cylindrocladium in inoculated trials.

Plants of the new Azalea differ from plants of the female parent, the selection YB-0335, in the following characteristics:

1. Plants of the new Azalea have better lower foliage retention than plants of the selection YB-0335.
2. Plants of the new Azalea are earlier to flower and flower more uniformly than plants of the selection YB-0335.
3. Plants of the new Azalea have much longer postproduction longevity than plants of the selection YB-0335.

Plants of the new Azalea differ from plants of the male parent, the selection YB-0815, in the following characteristics:

1. Plants of the new Azalea have semi-double flowers whereas plants of the selection YB-0815 have semi-double, hose-in-hose flowers.
2. Plants of the new Azalea flower have rich red-colored flowers whereas plants of the selection YB-0815 have coral-colored flowers.
3. Plants of the new Azalea have much longer postproduction longevity than plants of the selection YB-0815.

Plants of the new Azalea can be compared to the plants of the cultivar 'Prize', disclosed in U.S. Plant Pat. No. 3,795. However, in side-by-side comparisons conducted in Alva, Fla., plants of the new Azalea differed from plants of the cultivar 'Prize' in the following characteristics:

1. Plants of the new Azalea have semi-double flowers whereas plants of the cultivar 'Prize' have double, hose-in-hose flowers.

2. Plants of the new Azalea have lighter colored flowers than plants of the cultivar 'Prize'.

3. Plants of the new Azalea are more tolerant to low temperatures than plants of the cultivar 'Prize'.

BRIEF DESCRIPTION OF THE PHOTOGRAPHS

The accompanying colored photographs illustrate the overall appearance of the new Azalea. These photographs show the colors as true as it is reasonably possible to obtain in colored reproductions of this type. Colors in the photographs may differ slightly from the color values cited in the detailed botanical description, which accurately describe the colors of the new Azalea.

The photograph on the first sheet comprises a side perspective view of a typical flowering plant of 'Scarlet'.

The photograph on the second sheet is a close-up view of typical flowers and leaves of 'Scarlet'.

DETAILED BOTANICAL DESCRIPTION

The aforementioned and following observations, measurements, values, and comparisons describe plants grown in Alva, Fla. with three plants per 15-cm containers, in a polypropylene-covered shade house during the spring under commercial production conditions. During the production of the plants, day temperatures ranged from 13 to 37° C. and night temperatures ranged from 0 to 26° C. Plants were pinched at planting, pinched a second time about 12 weeks later, and pinched a third time about 12 weeks later. After sufficient flower bud development, plants were cooled at 3 to 5° C. for four weeks to break flower bud dormancy. Plants were subsequently forced into flower under commercial production conditions in a polyethylene-covered greenhouse. Plants used for the photographs and description were about one year old.

In the following description, color references are made to The Royal Horticultural Society Colour Chart except where general terms of ordinary dictionary significance are used.

Botanical classification:

*Botanical.*—*Rhododendron hybrida* 'Scarlet'.

*Commercial.*—Evergreen greenhouse-forcing type Azalea.

Parentage:

*Female or seed parent.*—Proprietary seedling selection of *Rhododendron hybrida* identified as code number YB-0335, not patented.

*Male or pollen parent.*—Proprietary seedling selection of *Rhododendron hybrida* identified as code number YB-0815, not patented.

Propagation:

*Type.*—By terminal vegetative cuttings.

*Time to initiate roots.*—Summer: About 35 days at temperatures of 24° C. Winter: About 42 days at temperatures of 24° C.

*Time to develop roots.*—Summer: About 63 days at temperatures of 24° C. Winter: About 77 days at temperatures of 24° C.

*Root description.*—Fine, fibrous, freely branching, white in color.

Plant description:

*Plant form and growth habit.*—Perennial, evergreen; outwardly spreading plant habit; inverted triangle; vigorous growth habit. Densely foliated. Freely flowering; numerous flowers per plant.

*Branching habit.*—Very freely branching; about four or five lateral branches develop after pinching (removal of terminal apex).

*Plant height, soil level to top of flowers.*—About 26 cm.

*Plant diameter, area of spread.*—About 51 cm.

*Lateral branch description.*—Length: About 21 cm. Diameter at base: About 7 mm. Texture: Young: Pubescent, fine brown hairs. Mature: Woody; pubescent, fine brown hairs. Color: Young: Close to 144A. Mature: Closest to between 165A and 166A.

*Foliage description.*—Arrangement: Alternate, single. Foliage retention: Very good foliage retention on plants of the new Azalea that have been in a box for six weeks during the cooling treatment. Length: About 4.1 cm. Width: About 2.4 cm. Shape: Broadly obovate. Apex: Cuspidate to mucronate. Base: Attenuate. Margin: Entire. Venation pattern: Pinnate. Texture, upper and lower surfaces: Leathery, tough, durable; pubescent. Luster: Upper surface: Glossy. Lower surface: Dull. Color: Young and mature foliage, upper surface: Much darker green than 147A. Young and mature foliage, lower surface: Close to 147B. Venation, upper surface: Main veins, close to 144A; lateral veins, same as lamina. Venation, lower surface: Main veins, close to 144A to 144B; lateral veins, same as lamina. Petiole: Length: About 1 cm. Diameter: About 2 mm. Texture: Upper surface: Smooth, glabrous. Lower surface: Pubescent. Color, upper and lower surfaces: Close to 144A to 144B.

Flower description:

*Natural flowering season.*—Spring after sufficient cool period. If forced, plants typically flower about 25 days after a four-week cooling treatment. Flowers persistent.

*Flower arrangement.*—Flowers arranged singly at terminals with usually about three flowers per apex; freely flowering. Flowers face upward and outward. Not fragrant.

*Flower appearance.*—Large semi-double flower form; rich red-colored petals.

*Flower diameter.*—About 10.25 cm.

*Flower depth.*—About 4.3 cm.

*Postproduction longevity.*—Under interior conditions, plants maintain good flower substance for about four weeks.

*Flower bud* (*before showing color*).—Rate of opening: About three to four days depending on temperatures. Length: About 1.3 cm. Diameter: About 7 mm. Shape: Ovoid. Texture: Covered with fine pubescence. Color: Close to 144A to 144B.

*Petals.*—Arrangement: Semi-double flower form; two whorls of five fused petals each; all stamens transformed into petal-like structures. Length: Outer whorl: About 5.7 cm. Inner whorl: About 5.1 cm. Width: Outer whorl: About 3.9 cm. Inner whorl:

About 3.4 cm. Shape: Beyond fused base, roughly orbicular to broadly ovate with rounded apex. Margin: Entire, undulate. Texture, upper and lower surfaces: Smooth, velvety. Color: When opening, upper and lower surfaces: Closest to but richer, darker and more intense than 53C. Fully opened, upper and lower surfaces: Closest to but richer, darker and more intense than 53C. Throat: Closest to but richer, darker and more intense than 53C. Spots on upper surface of lower three petals: Close to 53A.

*Sepals.*—Arrangement/appearance: One whorl of five small sepals, fused into a star-shaped calyx: leaf-like. Length: About 5.5 mm. Width: About 4 mm. Shape: Broadly ovate with sharply acute apex. Margin: Entire. Texture, upper and lower surfaces: Pubescent. Color: Upper surface: Close to 144A. Lower surface: Close to 144B to 144C.

*Peduncles.*—Length: About 1.7 cm. Diameter: About 2 mm. Angle: Upright to 50° from vertical. Strength: Flexible; strong. Texture: Pubescent. Color: Towards apex, 46A to 53A; towards base, 144A.

*Reproductive organs.*—Androecium: Stamens are usually transformed into petal-like structures. Petal-like stamens: Appearance: Irregular in size and shape. Length: About 4.7 cm. Width: About 2.9 cm. Shape: Roughly ovate with rounded apex, fused at base. Margin: Entire, undulate. Texture: Smooth, velvety. Color: Upper and lower surfaces: Closest to but richer, darker and more intense than 53C. Spots on upper surface of lower three petal-like stamens: Close to 53A. Gynoecium: Quantity of pistils: One per flower. Pistil length: About 4.3 cm. Style length: About 3.8 mm. Style diameter: Less than 1 mm. Style color: Close to 53A to 53B. Stigma diameter: About 2 mm. Stigma shape: Rounded. Stigma color: 59A. Ovary color: Close to 147A; heavily whiskered.

*Seed.*—Seed production has not been observed.

Weather/temperature tolerance: Plants of the new Azalea have been observed to be very tolerant to rain and wind. Plants of the new Azalea have been observed to tolerate temperatures from 0 to 37° C.

Disease resistance: In inoculated trials that were conducted in Alva, Fla. during the summers of 1997, 1999 and 2000, plants of the new Azalea have been observed to be resistant to infection by Cylindrocladium.

It is claimed:

1. A new and distinct Azalea plant named 'Scarlet', as illustrated and described.

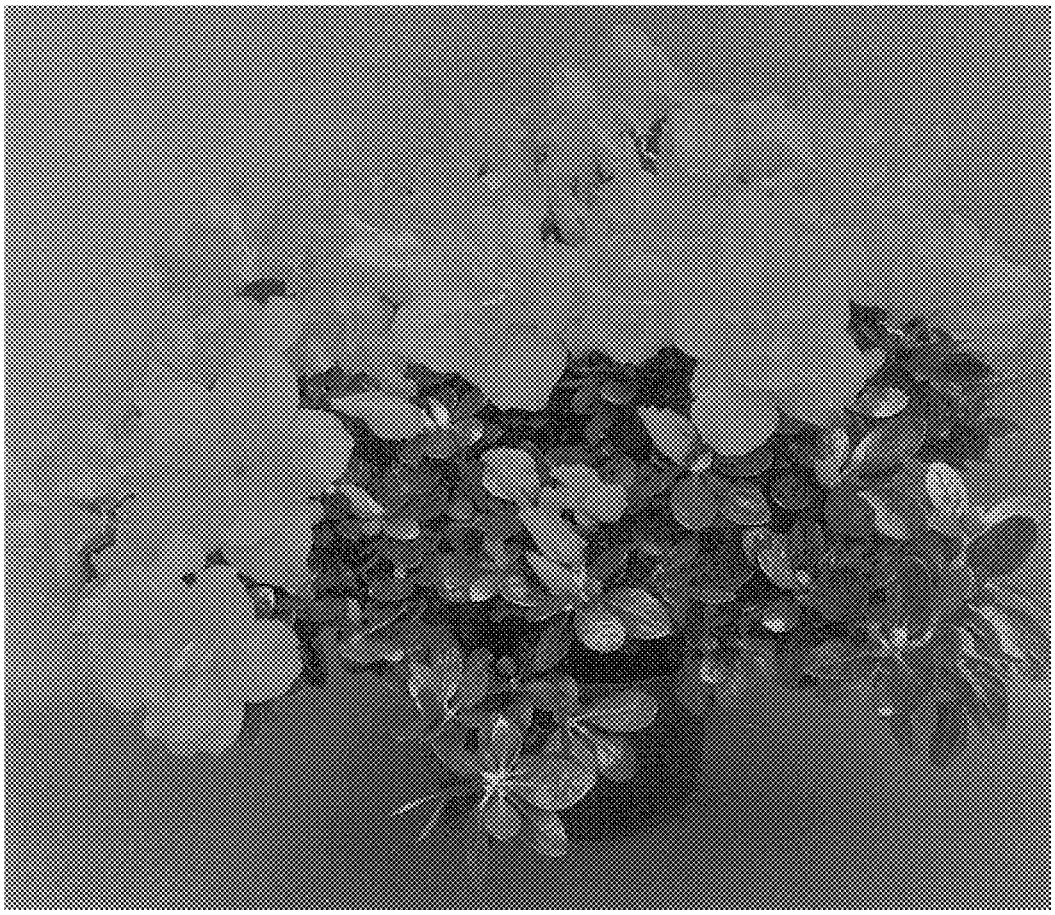

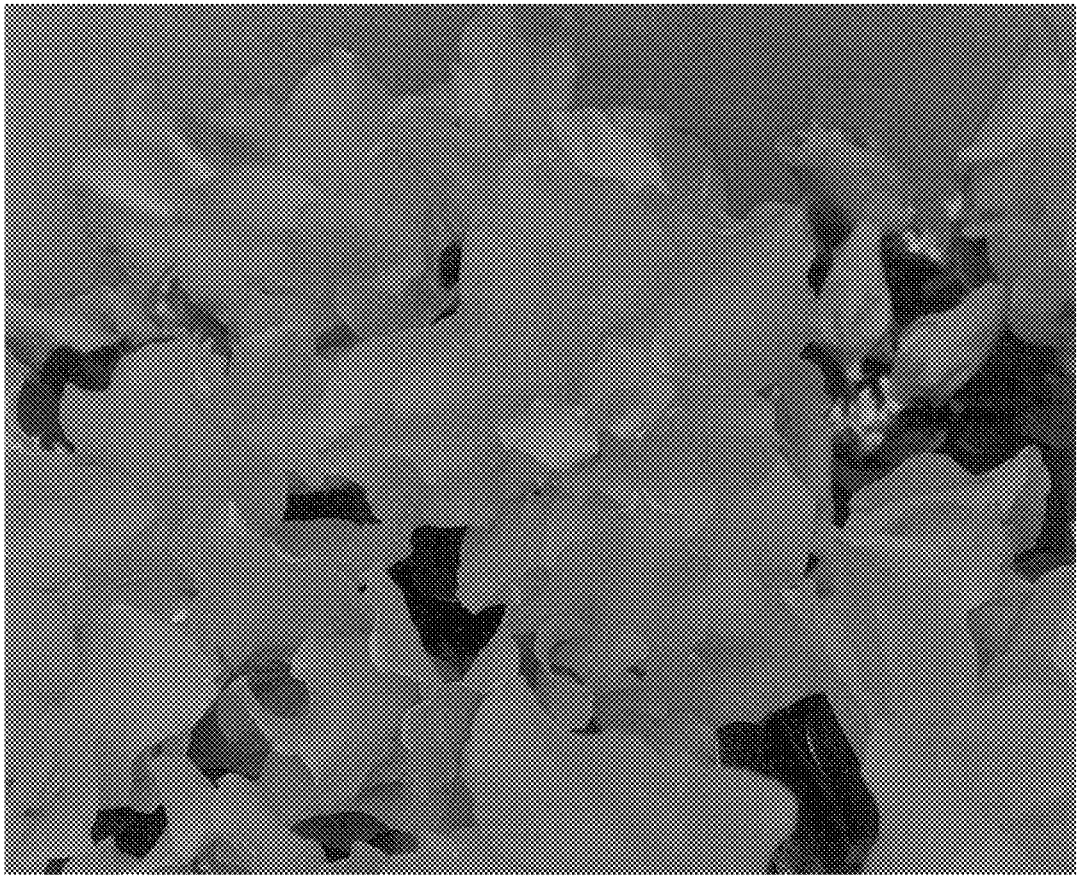

* * * * *